(12) United States Patent
Ohtake et al.

(10) Patent No.: US 7,221,451 B2
(45) Date of Patent: May 22, 2007

(54) MULTI-CHANNELED MEASURING METHOD AND APPARATUS FOR MEASURING SPECTRUM OF TERAHERTZ PULSE

(75) Inventors: Hideyuki Ohtake, Kariya (JP); Koichiro Tanaka, Kyoto (JP); Masaya Nagai, Kyoto (JP); Junpei Yamashita, Kyoto (JP); Kumiko Yamashita, Hyogo (JP)

(73) Assignee: Aisin Seiki Kabushiki Kaisha, Aichi-ken (JP)

( * ) Notice: Subject to any disclaimer, the term of this patent is extended or adjusted under 35 U.S.C. 154(b) by 377 days.

(21) Appl. No.: 10/926,351

(22) Filed: Aug. 26, 2004

(65) Prior Publication Data

US 2005/0179905 A1 Aug. 18, 2005

(30) Foreign Application Priority Data

Feb. 17, 2004 (JP) .............................. 2004-040230

(51) Int. Cl.
*G01J 3/28* (2006.01)
(52) U.S. Cl. ..................................... 356/326
(58) Field of Classification Search ................ 356/326
See application file for complete search history.

(56) References Cited

U.S. PATENT DOCUMENTS

2002/0067480 A1* 6/2002 Takahashi ................... 356/317
2003/0001558 A1* 1/2003 Zhang et al. ................. 324/96
2004/0196660 A1* 10/2004 Usami ........................ 250/330

FOREIGN PATENT DOCUMENTS

JP          2001-222035          8/2001

OTHER PUBLICATIONS

Kiyomi Sakai and Masanori Hangyo, "Terahertz Time Domain Spectroscopy and Imagin", Laser Kenkyu, vol. 30, No. 7, Jul. 2002, p. 376-384.
Zhiping Jiang and X.-C. Zhang, "Electro-optic Measurement of THz Field Pulse with a Chirped Optical Beam", Applied Physics Letters, vol. 72, No. 16, Apr. 20, 1998, pp. 1945-1947.

* cited by examiner

*Primary Examiner*—Samuel A. Turner
*Assistant Examiner*—Kara Geisel
(74) *Attorney, Agent, or Firm*—Sughrue Mion, PLLC

(57) ABSTRACT

A method for measuring a spectrum of a terahertz pulse includes generating a terahertz pulse using an ultrashort pulsed pumping light, generating a white light pulse using an ultrashort pulsed probe light, stretching and chirping the white light pulse modulating the chirped white light pulse such that the terahertz pulse and the chirped white light pulse irradiate into an electro-optic crystal synchronously, so that the chirped white light pulse is modulated by an electric field signal induced at the electro-optic crystal irradiated by the terahertz pulse, detecting a spectrum of chirped white light pulse modulated at the electro-optic modulating step by a multi-channeled detector, analyzing an electric field of the teraherz pulse irradiated to the electro-optic crystal from the spectrum of the chirped white light pulse detected by the multi-channeled spectrum detecting step, and transforming the analyzed electric field signal into a frequency spectrum of the terahertz pulse.

9 Claims, 5 Drawing Sheets

MULTI-CHANNELED MEASURING METHOD AND APPARATUS FOR MEASURING SPECTRUM OF TERAHERTZ PULSE

CROSS REFERENCE TO RELATED APPLICATIONS

This application is based on and claims priority under 35 U.S.C. § 119 to Japanese Patent Application 2004-040230, filed on Feb. 17, 2004, the entire content of which is incorporated herein by reference.

FIELD OF THE INVENTION

This invention generally relates to a multi-channel measuring method and an apparatus for measuring a frequency spectrum of a terahertz pulse.

BACKGROUND

Until now, terahertz wave spectroscopy in a time domain using a single channel detector is known (Reference 1 K. Sakai, et al., "Terahertz Time Domain Spectroscopy and Imaging," *Laser Kenkyu,* Vol. 30, No. 7, Jul. 2002, p. 376–384). Using this known method, a probe light has to be scanned using mechanically structured optical delay line for measuring all spectra, which makes measurement time consuming, and which makes real time measurement impossible.

Lately, a method for measuring an electric field signal of the terahertz pulse using a chirped light in a real time by a multi-channeled detector is investigated. (Reference 2: Zhiping Jiang and X. -C. Zhang "Electro-optic measurement of THz field pulses with a chirped optical beam", *Applied Physics Letters,* Vol. 72, No. 16, 20 Apr. 1998, pp. 1945–1947.) In this method, an ultra-short pulsed light from a laser apparatus is separated by a beam splitter to a pumping light and a probe light. The pumping light pumps an emitter for generating the terahertz pulse. On the other hand, the probe light is stretched and chirped by a grating pair. A ZnTe crystal is irradiated by the generated terahertz pulse and the stretched and chirped light. The probe light is modulated by an electro-optic effect induced from the electric field signal of the terahertz pulse. The transmitted probe light is dispersed into a spectrum by a diffraction grating, and detected by a multi-channeled detector array. A waveform detected by the detector array is the spectrum of the probe light modulated by the terahertz pulse. A horizontal axis of the waveform is a wavelength. The positively chirped probe light is extended in the time domain, and longer wavelength delays reaching a ZnTe crystal. Therefore, substantially, light delays for a certain time, depending on a wavelength thereof. Accordingly, the wavelength can be transformed into a delay time. Subtracting the spectrum of the probe light which is not modulated by the terahertz pulse from the modulated probe light yields the electric field signal of the terahertz pulse. Analyzing the electric field signal by Fourier transform yields the frequency spectrum of the terahertz pulse.

A frequency spectral range W and a resolution $\Delta W$ of the frequency spectral measurement of the terahertz pulse are written as $$W \sim (T_0 T_c)^{-1/2}/2 \quad (1)$$

$$\Delta W \sim 1/T_c \quad (2)$$

where $T_0$ is a pulse width of the probe light before being stretched and $T_c$ is a pulse width of the probe light after being stretched. According to equation (1), for increasing the spectral range of the terahertz pulse (increasing W), $T_c$ should be decreased. According to equation (2), for increasing the resolution of the frequency spectral measurement of the terahertz pulse (decrease $\Delta W$), $T_c$ should be increased. There is a trade-off between the frequency spectral range and the resolution of the frequency spectral measurement of the terahertz pulse. Therefore, wide spectral range and high resolution can not be obtained simultaneously.

As mentioned above, in known multi-channeled measuring method for measuring the spectrum of the terahertz pulse, when the spectral range is widen, the resolution of the measurement is lowered. On the other hand, when the resolution of the measurement is raised, the spectral range is narrowed.

A need thus exists for a multi-channeled measuring method and a multi-channeled measuring apparatus for measuring a spectrum of a terahertz pulse with both wide spectral range and high resolution.

SUMMARY OF THE INVENTION

According to an aspect of the present invention, a multi-channeled measuring method for measuring a spectrum of a terahertz pulse includes the steps of a terahertz pulse generating step for generating a terahertz pulse by using an ultrashort pulsed pumping light, a white light generating step for generating a white light pulse by using an ultrashort pulsed probe light, a stretching step for stretching and chirping the white light pulse generated at the white light pulse generating step, an electro-optic modulating step for modulating the chirped white light pulse stretched and chirped at the stretching step in such a manner that the terahertz pulse and the chirped white light pulse irradiate into an electro-optic crystal synchronously, so that the chirped white light pulse is modulated by an electric field signal induced at the electro-optic crystal irradiated by the terahertz pulse, a multi-channeled spectral detecting step for detecting a spectrum of chirped white light pulse modulated at the electro-optic modulating step by a multi-channeled detector, an electric field signal analyzing step for analyzing an electric field of the terahertz pulse irradiated to the electro-optic crystal from the spectrum of the chirped white light pulse detected by the multi-channeled spectrum detecting step, and a Fourier transforming step for transforming the electric field signal analyzed by the electric field signal analyzing step into a frequency spectrum of the terahertz pulse.

According further aspect of the present invention, a multi-channeled measuring apparatus for measuring a spectrum of a terahertz pulse includes a terahertz pulse source pumped by an ultrashort pulsed pumping light and generating a terahertz pulse, a white light pulse source generating a white light pulse by being irradiated by an ultrashort pulsed probe light, a stretching means for stretching and chirping the white light pulse generated by the white light pulse source, an electro-optic crystal irradiated by the terahertz pulse generated by the terahertz pulse source and the chirped white light pulse stretched and chirped by the stretching means overlapped to the terahertz pulse in a time domain for modulating the chirped white light pulse by an electric field signal induced by the terahertz pulse, a multi-channeled spectral detecting means for detecting a spectrum of the chirped white light pulse modulated by the electro-optic crystal, and an analyzing means for analyzing the electric field signal of the terahertz pulse irradiated to the electro-optic crystal from the spectrum of the chirped white light pulse detected by the multi-channeled spectral detector, and obtaining a frequency spectrum of the terahertz pulse by using Fourier transform of the analyzed electric field signal.

According to further aspect of the present invention, a multi-channeled measuring method for measuring a spectrum of a terahertz pulse includes the steps of a terahertz pulse generating step for generating a terahertz pulse by pumping a terahertz pulse source by an ultrashort light pulsed pumping light, a white light generating step for generating a white light pulse by irradiating a white light pulse source by an ultrashort pulsed probe light, a stretching step for stretching and chirping a white light pulse generated by the white light pulse generating step, an electro-optic modulating step for modulating the chirped white light pulse stretched and chirped at the stretching step in such a manner that the terahertz pulse and the chirped white light pulse irradiate into an electro-optic crystal synchronously, so that the chirped white light pulse is modulated by an electric field signal induced at the electro-optic crystal irradiated by the terahertz pulse, a multi-channeled spectral detecting step for detecting the modulated chirped white light pulse modulated by the electro-optic modulating step by a multi-channeled detector, an electric field signal analyzing step for analyzing the electric field signal of the terahertz pulse by subtracting a spectral data of the chirped white light pulse from a spectral data of the modulated chirped white light pulse detected by the multi-channeled spectral detecting step, and a Fourier transforming step for transforming the electric field signal analyzed by the electric field signal analyzing step into a frequency spectrum of the terahertz pulse.

BRIEF DESCRIPTION OF THE DRAWINGS

The foregoing and additional features and characteristics of the present invention will become more apparent from the following detailed description considered with reference to the accompanying drawings, wherein.

DETAILED DESCRIPTION

Figure 1:
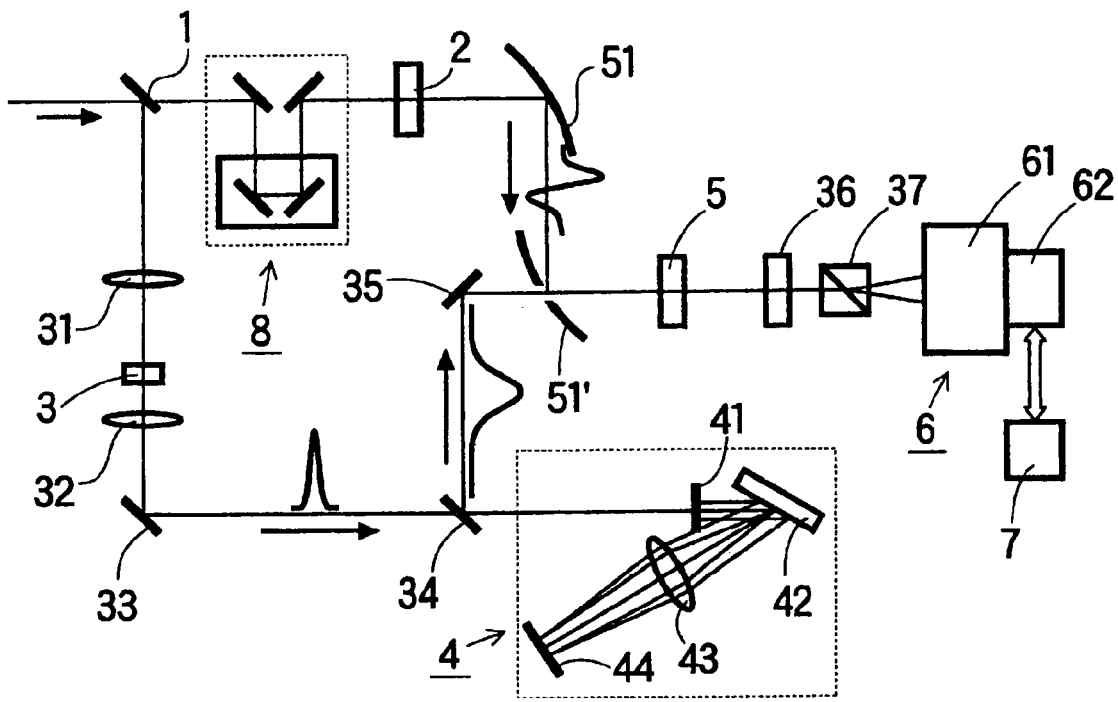
FIG. 1 shows a schematic diagram of a multi-channeled measuring apparatus for measuring a spectrum of a terahertz pulse in a first embodiment.

Embodiments of the present invention will be explained with reference to the illustrations of the drawing figures as follows.

According to a first embodiment of the present invention, a multi-channeled measuring apparatus for measuring a spectrum of a terahertz pulse includes a dividing means 1 for dividing an ultrashort light pulse into a pumping light and a probe light, a terahertz pulse source 2 pumped by the pumping light serving as an ultrashort pumping light divided by the dividing member for generating the terahertz pulse, a white light pulse source 3 irradiated by the probe light serving as an ultrashort pulsed probe light divided by the dividing member for generating a white light pulse, a stretching means 4 for stretching and chirping the white light pulse generated by the white light source 3, an electro-optic crystal 5 irradiated by overlap of the terahertz pulse generated by the terahertz pulse source 2 and the white light pulse stretched and chirped by the stretcher 4 for modulating the chirped white light pulse by an electro-optic effect by an electric field signal of the terahertz pulse, a multi-channeled spectral detecting means 6 for detecting the chirped white light pulse modulated by the electro-optic crystal 5 by a multi-channeled detector, and an analyzing means 7 for analyzing the electric field signal of the terahertz pulse by which the electro-optic crystal 5 is irradiated and for Fourier transforming the analyzed electric field signal into a frequency spectrum of the terahertz pulse.

The ultrashort light pulse is generated by a regenerative amplifier system of a Ti: sapphire laser. The ultrashort light pulse is 100 fs in pulse width, 800 nm in wavelength, 1 mJ/pulse in pulse energy, 1 kHz in pulse repetition frequency. A characteristics of the ultrashort light pulse is not limited to that of the pulse mentioned above. More preferable, pulse energy may be larger, because larger pulse energy enables to improve a signal-to-noise ratio of the spectral measurement.

The dividing means 1 may be a half-mirror typed splitter as in the embodiment, or a polarizing beam splitter.

The terahertz pulse source 2 is pumped by the ultrashort light pulse and generates the terahert pulse. A photoconductive switch semiconductor (a metallic antenna is formed on low temperature grown Gallium Arsenide (LT-GaAs), a bulk semicoductor such as InAs, a quantum well semiconductor, a non-linear optical crystal, a high-temperature superconductor, or the like, may be used for the terahertz pulse source 2. Normally, ultrashort light pulse is focused on the terahertz pulse source 2 for increasing efficiency and intensity of the terahertz pulse generation. The photoconductive switch semiconductor has high efficiency of the terahertz pulse generation. However, if the photoconductive switch semiconductor is irradiated by intense laser light for increasing generating power, the photoconductive switch semiconductor will be broken by the laser light. The photoconductive switch semiconductor will worsen also by being used for a long time. InAs has highest efficiency of the terahertz generation among bulk semiconductors. Particularly, generation efficiency and generation intensity are increased by applying a high magnetic field. In the embodiment, a non-linear optical crystal, ZnTe, is used for the terahertz pulse source 2.

A water cell and an optical fiber, or the like, are used as the white light pulse source 3 irradiated by the probe light and generating the white light pulse. When the water or the optical fiber is irradiated by the ultrashort light pulse, white light pulse having broad frequency spectrum is induced by a non-linear optical effect such as an induced Raman scattering. In the embodiment, the water cell is used for the white light pulse source 3.

If $\Delta\omega > \Delta\omega_0$, where $\Delta\omega_0$ is spectral width of the probe light and $\Delta\omega$ is spectral width of the probe light after transmitted through an element assumed to be the white light source, it is assumed that the probe light is changed into the white light. Thus, the light pulse with spectral width $\Delta\omega$ is defined as the white light pulse. The spectral width $\Delta\omega$ is preferred to be as wide as possible because the spectral width becomes broader. However, if the spectral width became too much broader, an energy of the probe light would be dispersed and the detection of the spectrum of the terahertz pulse would be impossible. Therefore, the spectral width of the probe light should be determined in a preferable range with consideration about a balance between the spectral width and the energy.

The stretching means 4 stretches and chirps the white light pulse generated by the white light pulse source 3. A bulk grating, a prism, a holographic grating, a fiber grating may be used for the stretching means 4. In the embodiment, a stretching means including a bulk grating 42 and a collimating lens 43 is used.

A ZnTe crystal is used for the electro-optic crystal 5 for modulating the white light pulse by the electric field signal of the terahertz pulse.

A multi-channeled spectral detector 6 detecting the spectrum of the white light pulse modulated by the electro-optical crystal 5 by multi-channeled detector includes a spectrometer 61 and a CCD camera 62. The spectrometer used in the embodiment is a grating type spectrometer of which focal length is 50 cm.

A CPU is used for the analyzing means 7 for conducting flexible analysis.

The probe light pulse divided by a beam splitter 1 (serving as the dividing means 1) is focused on the water cell 3 (serving as the white light pulse source 3) by a lens 31 for generating the white light pulse from the water by a non-linear optical effect. The white light pulse stretched and chirped by the stretching means 4 is introduced to ZnTe 5 (serving as the electro-optic crystal 5) via a half mirror 34, a bending mirror 35, and a hole of a holed off-axis parabolic mirror 51'.

On the other hand, the pumping light pulse divided by the beam splitter 1 is delayed by a delay line 8 for predetermined time introducing to a ZnTe 2 (serving as the terahertz pulse source 2) for generating the terahertz pulse. The generated terahertz pulse is collimated by an off-axis parabolic mirror 51, and focused by the holed off-axis parabolic mirror 51' on the ZnTe 5. The delay line 8 is used for introducing an overlap of the white light pulse and the terahertz pulse in the time domain to the ZnTe 5.

The chirped white light is modulated while transmitting through the ZnTe 5 by a Pockels effect induced by the electric field signal of the terahertz pulse introduced to the ZnTe 5. An intensity of the modulated white light pulse is adjusted by a wavelength plate 36 and a polarizing beam splitter 37 to a predetermined value and the spectrum thereof is detected by the spectral detector 6.

The frequency spectrum of the terahertz pulse is obtained by being analyzed by a CPU as follows. The electric field signal of the terahertz pulse is obtained by subtracting a spectral data of the chirped white light pulse under the condition that the terahertz pulse is not introduced to the ZnTe 5 from the spectral data of the chirped white light pulse mentioned above. The frequency spectrum of the terahertz pulse is obtained by analyzing the electric field signal by Fourier transform.

Figure 2:
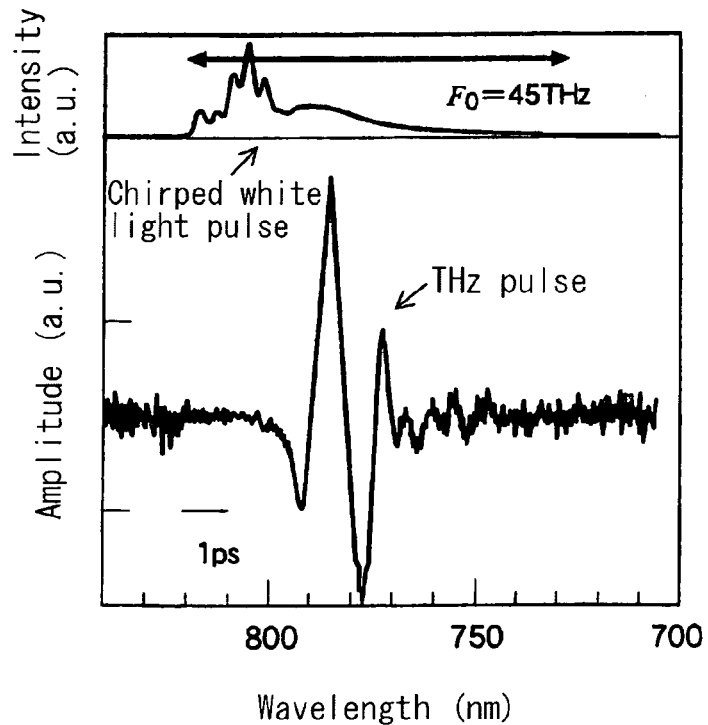
FIG. 2 shows a spectrum of a chirped white light pulse and an waveform of an electric field signal of a terahertz pulse measured by the multi-channeled measuring apparatus for measuring the spectrum of the terahertz pulse in the first embodiment.
Figure 3:
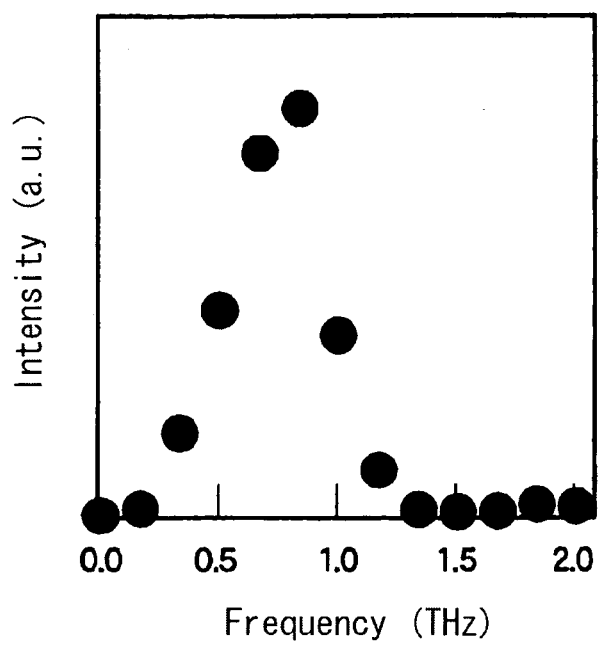
FIG. 3 shows a frequency spectrum of the terahertz pulse obtained by analyzing the electric field signal by Fourier transform.
Figure 4:
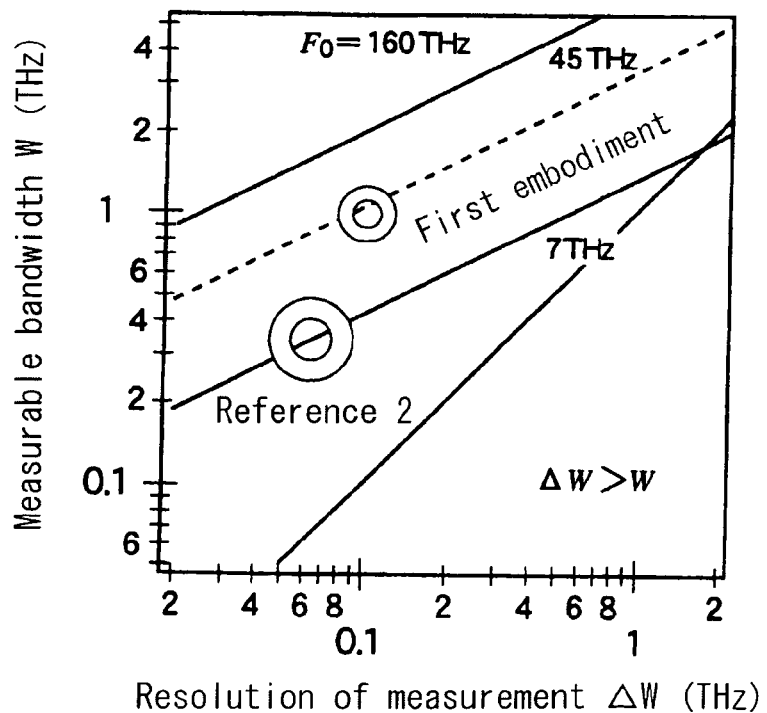
FIG. 4 shows a relation between a measurable bandwidth and a resolution of the measurement of the terahertz pulse as a parameter of a frequency bandwidth of a probe light pulse.

FIGS. 2 and 3 show a result measured every one pulse by the apparatus according to the first embodiment. A wavelength indicated on a horizontal axis of FIG. 2 can be calibrated into a time by changing a timing of the terahertz pulse reaching the ZnTe 5 by the optical delay line 8. A horizontal bar shown in FIG. 2 shows 1 ps on calibrated time scale. An upper part of FIG. 2 shows the spectrum of the chirped white light pulse. The spectrum ranges from about 730 nm–820 nm. A width of a frequency spectral range $F_0$ is estimated at 45 THz. A lower part of FIG. 2 shows the electric field signal of the terahertz pulse obtained by subtracting the spectrum of the chirped white light pulse measured in advance under condition that the terahertz pulse is not introduced to the ZnTe 5 from the spectrum of the chirped white light pulse shown in upper part of FIG. 2. FIG. 3 shows the frequency spectrum of the terahertz pulse obtained by analyzing the electric field signal of the terahertz pulse in FIG. 2 by Fourier transform. A resolution $\Delta W$ and a measurable bandwidth W of the frequency spectral measurement of the terahertz pulse are estimated at 0.12 THz, 0.9 THz respectively. FIG. 4 shows a comparison of the resolution and the measurable bandwidth of the measurement with that of a known art. The measurable bandwidth becomes broader than that of the known art as predicted in theory.

The result mentioned above is obtained by measuring every one pulse. A signal-to-noise ratio can be improved by measuring every 10 pulses. A close value of the measurable bandwidth (W=1.1 THz) to a theoretical value is obtained by measuring every 10 pulses.

Figure 5:
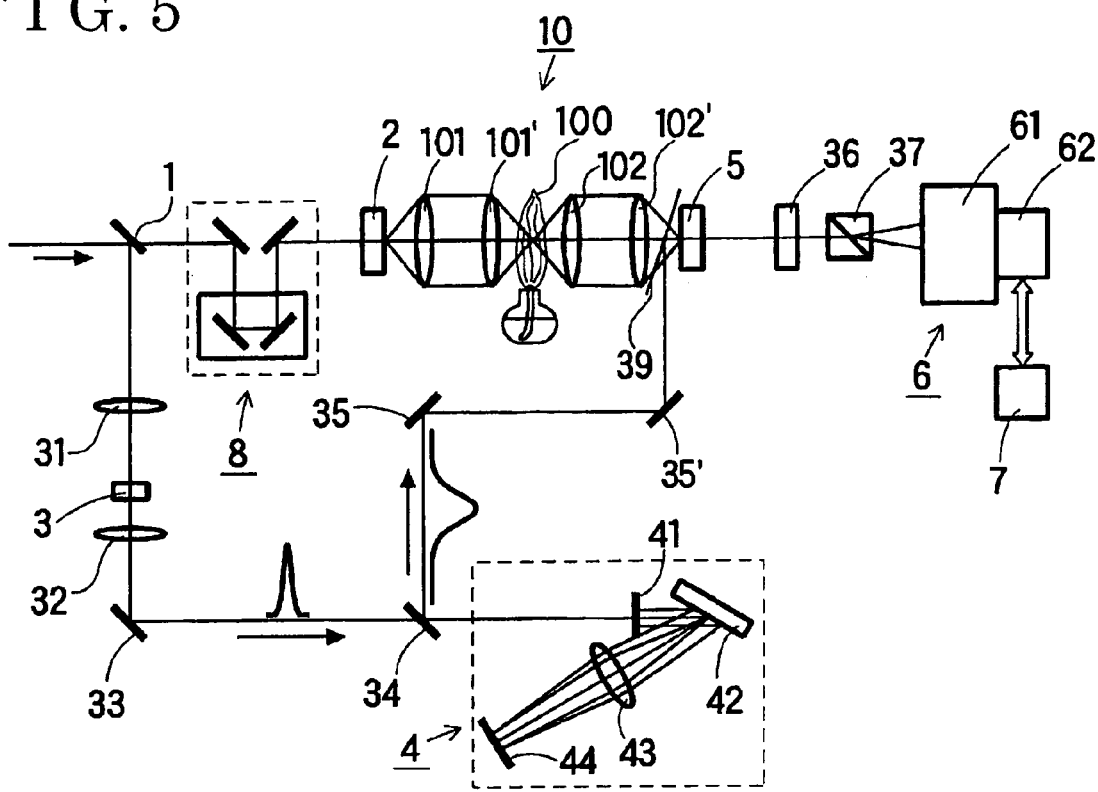
FIG. 5 shows a schematic diagram of a multi-channeled measuring apparatus for measuring a spectrum of a terahertz pulse in a second embodiment.

A second embodiment of the present invention will be explained with reference to the illustrations of the drawing figures as follows. FIG. 5 shows a schematic diagram of a multi-channeled measuring apparatus for measuring a spectrum of a terahertz pulse in the embodiment. In the second embodiment, an irradiating means 10 for irradiating the sample by the terahertz pulse is added to the apparatus in the first embodiment shown in FIG. 1. The apparatus in the second embodiment can measure a time profile of the spectrum of the terahertz pulse transmitted through and influenced by the flame 100. Because elements except the irradiating means 10 are almost the same in the embodiment 1, these elements will not be explained. The irradiating means 10 includes condenser lenses 101, 101' for collecting the terahertz pulse generated from the ZnTe 2 and condenser lenses 102, 102' for focusing the terahertz pulse on the ZnTe 5. The flame 100 is positioned between the condenser lenses 101' and 102 at the confocal position thereof. The chirped white light pulse is reflected by a dichroic mirror 39 for irradiating the ZnTe 5.

Figure 6:
FIG. 6 shows a pattern diagram for explaining results measured by the multi-channeled measuring apparatus for measuring the spectrum of the terahertz pulse in the second embodiment.
Figure 6:
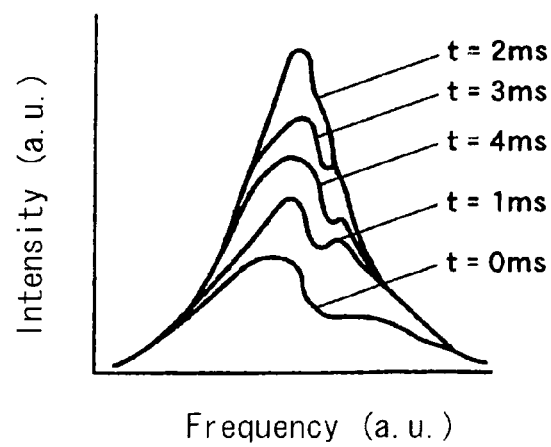
Figure 7:
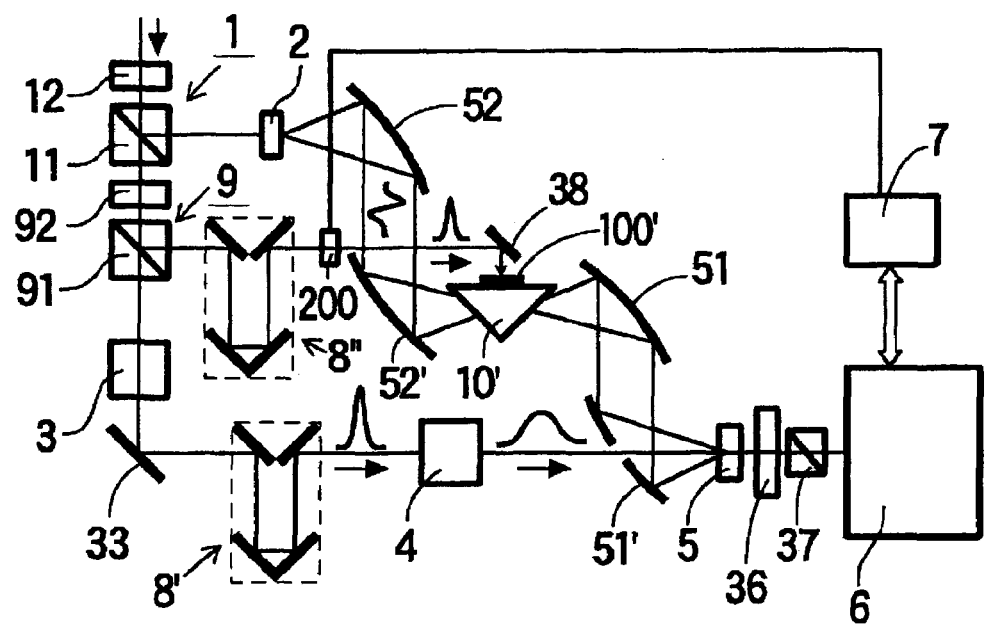
FIG. 7 shows a schematic diagram of a multi-channeled measuring apparatus for measuring a spectrum of a terahertz pulse in a third embodiment.

FIG. 6 shows a pattern diagram for explaining measured results. A pulse repetition frequency of an ultrashort light pulse in the embodiment is 1 kHz. Therefore, the spectrum is measured every 1 ms as shown in upper part of FIG. 6. A lower part of FIG. 6 shows the spectra of the terahertz pulse measured at these timings shown in the upper part of the FIG. 6. A horizontal axis of the lower part of FIG. 6 indicates the frequency of the terahertz pulse. A time profile of the flame 100 as sample (excitation and relaxation between rotational levels of $CO_2$ and $H_2O$ in the flame, or the like) can be measured by measuring the time profile of the spectrum of the terahertz pulse in real time (1 ms). In the embodiment, the chirped white light pulse is used as the probe light. Therefore, the resolution of the measured spectrum is high and the bandwidth of the measured spectrum is broad. Accordingly, the time profile of the sample can be measured in broad spectral range and at high resolution.

A third embodiment of the present invention will be explained with reference to the illustrations of the drawing figures as follows. In the third embodiment, a reflective typed irradiating means 10' is added to the apparatus in the first embodiment. In the third embodiment, a sample 100' is excited by an excitation light extracted by a extracting means 9 for extracting the excitation light from the probe light divided by the dividing means 1. Same number is assigned to the same components as in the embodiment 1 in order to skip an explanation for them. The dividing means 1 for dividing the ultrashort light pulse into the pumping light pulse and the probe light pulse includes a polarizing beam splitter 11 and a wavelength plate 12. The extracting means 9 for extracting excitation light includes a polarizing beam splitter 91 and a wavelength plate 92. A gate 200 is an electric shutter for transmitting one extracted excitation light pulse at a predetermined timing. The irradiating means 10' is an isosceles shaped attenuated total reflection (ATR) prism. A sample 100' is put on a base side surface of the isosceles shaped prism. In this embodiment, the sample 100' is an InAs semiconductor crystal.

The probe light pulse divided by the dividing means 1 is introduced to the water cell 3 for inducing the white light pulse by the non-linear optical effect. The induced white light pulse is delayed by a bending mirror 33 and an optical delay line 8' introducing to the stretching means 4. The white light pulse stretched and chirped by the stretching means 4 is introduced to the ZnTe 5 via a hole of holed off-axis parabolic mirror 51'.

The pumping light pulse divided by the dividing means 1 is introduced to the ZnTe 2 for generating the terahertz pulse. The generated terahertz pulse is collimated by an off-axis parabolic mirror 52 and focused on the base side surface of the isosceles shaped ATR prism 10' by an off-axis parabolic mirror 52' via one surface of leg side surfaces of the ATR prism in order that the terahertz pulse is totally reflected by the base side surface of the ATR prism 10'. The base side surface of the ATR prism is contacting with one surface of InAs 100'. When the terahertz pulse is totally reflected, an evanescent wave is formed near the surface of the ATR prism 10' contacting with the InAs 100'. The evanescent wave interacts with the InAs 100'. The totally reflected terahertz pulse including information of the interacted evanescent wave is emitted from the other surface of the leg side surfaces of the ATR prism 10', collimated by an off-axis parabolic mirror 51, and focused on the ZnTe 5 by a holed off-axis parabolic mirror 51'. The excitation light pulse extracted by the extracting means 9 is delayed by an optical delay line 8" by the predetermined time, converted into one pulse at predetermined timing by the gate 200, and introduced to the InAs 100' via a bending mirror 38.

The optical delay line 8' delays the white light pulse for the predetermined time introducing the overlap of the white light pulse and the terahertz pulse in the time domain to the ZnTe 5. The optical delay line 8" delays the excitation light pulse for the predetermined time introducing the overlap of the terahertz pulse and the excitation light pulse in the time domain to the InAs 100'.

Figure 8:
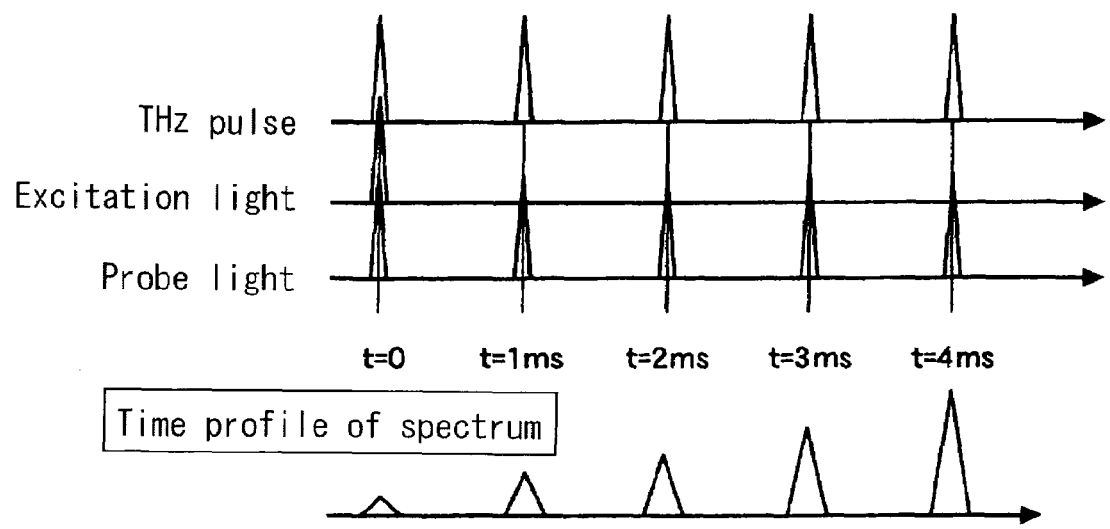
FIG. 8 shows a chronograph for explaining results measured by the multi-channeled measuring apparatus for measuring the spectrum of the terahertz pulse in the third embodiment.
Figure 9:
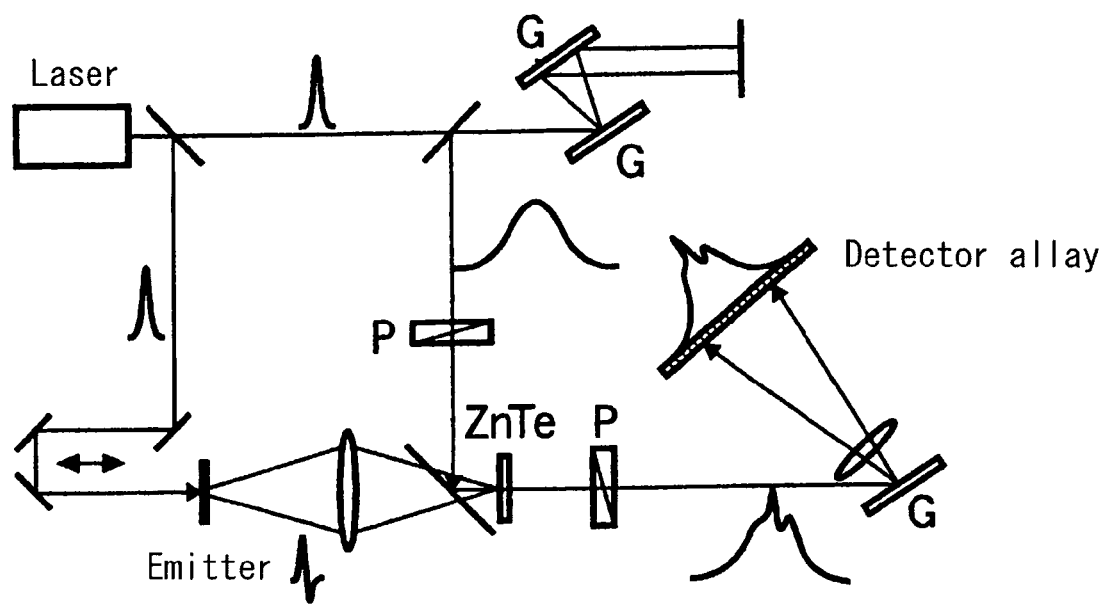
FIG. 9 shows a schematic diagram of a known multi-channeled measuring apparatus for measuring an electric field signal of a terahertz wave.

FIG. 8 shows a chronograph for explaining a measured results of the embodiment. An upper part of FIG. 8 shows timings of irradiating the ZnTe 5. A horizontal axis of the upper part of FIG. 8 indicates time. An upper line, a middle line, a lower line indicate irradiating timings by the terahertz pulse, the excitation light pulse, and the probe light pulse respectively. The ZnTe 5 is irradiated by excitation light pulse at first one time. The ZnTe 5 is irradiated by the terahertz pulse and the probe light pulse every 1 ms because the repetition frequency of the terahertz pulse and the probe light pulse are 1 kHz. A lower part of FIG. 8 shows spectra of the terahertz pulse obtained every 1 ms. Relaxation process of the plasmon excited at an initial time (t=0) by the excitation light pulse in the InAs 100' can be measured every 1 ms through the time profile of the spectra.

According to an aspect of the present invention, the resolution of the measurement becomes high and the spectral range of the measurement becomes wide. From equations (1) and (2), using $F_0$ as a frequency spectral range of the probe light, where $F_0 \sim 1/T_0$, the frequency spectral range W and the resolution $\Delta W$ of the frequency spectral measurement of the terahertz pulse are $$W \sim (F_0 \Delta W)^{1/2} 2 \qquad (3)$$

$$\Delta W \sim 4W^2/F_0 \qquad (4)$$

FIG. 4 shows a relation between W and $\Delta W$ in equation (3), using $F_0$ as a parameter. According to FIG. 4 and equations (3) and (4), the spectral range becomes wider (W is increased) and the resolution of the measurement becomes higher ($\Delta W$ is decreased) when $F_0$ is increased. Accordingly, by increasing $F_0$, the resolution of the measurement becomes high and the spectral range of the measurement becomes high.

According to further aspect of the present invention, because the white light pulse of wide spectral range $F_0$ is used as probe light, a wide measurable width of the spectral range of the terahertz pulse and high resolution of the measurement may be available in the multi-channeled measuring apparatus for measuring the spectrum of the terahertz pulse.

According to further aspect of the present invention, because the spectrum of the probe light is measured by the multi-channeled detector and the frequency spectrum of the terahertz pulse is analyzed every one pulse, the real time measurement may be possible. Further, because terahertz pulse irradiated to the sample is influenced by the sample, the real time measurement of the frequency spectrum of the terahertz pulse influenced by the sample provides the time profile of the sample in real time. Accordingly, a time profile of a flame, a moving object, a light induced chemical reaction of a semiconductor and a protein can be measured in real time.

According to further aspect of the present invention, because the spectra data measured every one pulse of the white light pulse are stored and the electric field is analyzed every plural pulses, the signal-to-noise ratio of the spectral measurement can be improved.

According to further aspect of the present invention, a synchronizing of the terahertz pulse generated by the terahertz pulse source 2 with the chirped white light pulse stretched and chirped by the stretching means 4 may be easy with the dividing means 1 for dividing one ultrashort light pulse into the pumping light pulse and the probe light pulse.

The principles, preferred embodiment and mode of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the sprit of the present invention. Accordingly, it is expressly intended that all such variations, changes and equivalents which fall within the spirit and scope of the present invention as defined in the claims, be embraced thereby.

The invention claimed is:

1. A multi-channeled measuring apparatus for measuring a spectrum of a terahertz pulse comprising:
    a terahertz pulse source pumped by an ultrashort pulsed pumping light and generating a terahertz pulse;
    a white light pulse source generating a white light pulse by being irradiated by an ultrashort pulsed probe light;
    a stretching means for stretching and chirping the white light pulse generated by the white light pulse source;
    an electro-optic crystal irradiated by the terahertz pulse generated by the terahertz pulse source and the chirped white light pulse stretched and chirped by the stretching means overlapped to the terahertz pulse in a time domain for modulating the chirped white light pulse by an electric field signal induced by the terahertz pulse;
    a multi-channeled spectral detecting means for detecting a spectrum of the chirped white light pulse modulated by the electro-optic crystal; and
    an analyzing means for analyzing the electric field signal of the terahertz pulse irradiated to the electro-optic crystal from the spectrum of the chirped white light pulse detected by the multi-channeled spectral detecting means, and obtaining a frequency spectrum of the terahertz pulse by using Fourier transform of the analyzed electric field signal.

2. The multi-channeled measuring apparatus for measuring the spectrum of the terahertz pulse according to claim 1, further comprising:
    a dividing means for dividing one ultrashort light pulse into the pumping light and the probe light.

3. The multi-channeled measuring apparatus for measuring the spectrum of the terahertz pulse according to claim 1, wherein
    the pumping light and the probe light are continuously generated, and the frequency spectrum of the terahertz pulse is analyzed every one pulse by the analyzing means.

4. The multi-channeled measuring apparatus for measuring the spectrum of the terahertz pulse according to claim 2, wherein
    the pumping light and the probe light are continuously generated, and the frequency spectrum of the terahertz pulse is analyzed every one pulse by the analyzing means.

5. The multi-channeled measuring apparatus for measuring the spectrum of the terahertz pulse according to claim 1, wherein
    the pumping light and the probe light are continuously generated, and data of the white light pulse are stored every one pulse and the electric field signal is analyzed every plural pulses and the analyzed electric field signal is analyzed by Fourier transform every plural pulses for obtaining the frequency spectrum of the terahertz pulse.

6. The multi-channeled measuring apparatus for measuring the spectrum of the terahertz pulse according to claim 2, wherein
    the pumping light and the probe light are continuously generated, and data of the white light pulse are stored every one pulse and the electric field signal is analyzed every plural pulses and the analyzed electric field signal is analyzed by Fourier transform every plural pulses for obtaining the frequency spectrum of the terahertz pulse.

7. The multi-channeled measuring apparatus for measuring the spectrum of the terahertz pulse according to claim 1, further comprising:
    an irradiating means provided between the terahertz pulse source and the electro-optic crystal for irradiating a sample by the terahertz pulse generated from the terahertz pulse source.

8. The multi-channeled measuring apparatus for measuring the spectrum of the terahertz pulse according to claim 5, further comprising:
    an irradiating means provided between the terahertz pulse source and the electro-optic crystal for irradiating a sample by the terahertz pulse generated from the terahertz pulse source.

9. The multi-channeled measuring apparatus for measuring the spectrum of the terahertz pulse according to claim 6, further comprising:
    an irradiating means provided between the terahertz pulse source and the electro-optic crystal for irradiating a sample by the terahertz pulse generated from the terahertz pulse source.

* * * * *